United States Patent
Kamal et al.

(10) Patent No.: US 7,374,926 B2
(45) Date of Patent: May 20, 2008

(54) ENANTIOCONVERGENT CHEMOENZYMATIC SYNTHESIS OF (R)-γ-AMINO-β-HYDROXYBUTYRIC ACID ((R)-GABOB)

(75) Inventors: Ahmed Kamal, Hyderabad (IN); Gollapalli B. Ramesh Khanna, Hyderabad (IN); Krishnaji Tadiparthi, Hyderabad (IN); Ramu Rondla, Hyderabad (IN)

(73) Assignee: Council of Scientific and Industrial Research (IN)

( * ) Notice: Subject to any disclaimer, the term of this patent is extended or adjusted under 35 U.S.C. 154(b) by 136 days.

(21) Appl. No.: 11/022,275

(22) Filed: Dec. 23, 2004

(65) Prior Publication Data

US 2006/0141606 A1  Jun. 29, 2006

(51) Int. Cl.
*C12P 41/00* (2006.01)
*C12P 13/00* (2006.01)
*C12P 7/00* (2006.01)
*C12P 7/04* (2006.01)
*C12P 7/52* (2006.01)

(52) U.S. Cl. ............ 435/280; 435/128; 435/132; 435/141; 435/155

(58) Field of Classification Search .......... None
See application file for complete search history.

(56) References Cited

U.S. PATENT DOCUMENTS 4,963,492 A * 10/1990 Keller et al. ............... 435/280
5,534,436 A * 7/1996 Seufer-Wasserthal et al. .... 435/280

FOREIGN PATENT DOCUMENTS

JP        51100026        9/1976

OTHER PUBLICATIONS

Jung, M.E., et al. JACS, 1980, 102, 6304-11.*
Itoh, T.,et al. JOC 1991, 56, 1521-24.*
Kazlauskas, R.J., et al. JOC 1991, 56, 2656-65.*
JP 51100026 A, Sep. 1976, Kurano, Masayasu, et al., English Translation, pp. i,1-21.*
JP 51100026 A, Sep. 1976, Kurano, Masayasu, et al., CAS Abstract, AN:86:89207, 1 page.*
Otsuka, M. et al.; "Measurement of γ-Aminobutyric Acid in Isolated Nerve Cells of Cat Central Nervous System," J. Neurochem, 18, 287 (1971).
Otsuka, M. et al., "Application of Enzymatic Cycling to the Measurement of Gamma-Aminobutyric Acid in Single Neurons of the Mammalian Central Nervous System," Advances in Biochemical Psychopharamacology Raven: New York, vol. 6, pp. 61 (1972).
Brehm, L. et al., "Heterocyclic GABA Agonists. Synthesis and Crystal Structure of (RS)-5-(N-t-Butyloxycarbonylaminomethyl)-3-oxoisoxazolidine-2-carboxamide, a Derivative of Dihydromuscimol," J. Chem. Soc. Perkin Trans I, 1459 (1983).
Takano, S. et al., "Practical Synthesis of (R)-Y-Amino-B-Hydroxybutanoic Acid (Gabob) From (R)-Epichlorohydrin," Tetrahedron Lett., 28, 1783 (1987).
Fritz, I. et al., "Specificity of carnitine action on fatty acid oxidation by heart muscle," Am. J. Physiol., 202, 117 (1962).
Schroeder et al., "Do Patients in Whom Myocardial Infarction Has Been Ruled Out Have a Better Prognosis After Hospitalization Than Those Surviving Infarction?", N. Engl. J. Med. 303, (1980)p.1. (Abstract, Introduction, Methods (*p. 1 only) ).
McGarry, J. D. et al., "Regulation of Hepatic Fatty Acid Oxidation and Ketone Body Production," Ann. Rev. Biochem, 49, 395 (1980).
Kurano et al., "Optical resolution of 4-amino-3-hydroxybutyramide," Chem. Abstr. 86, 89207u (1977). (no translation: only title and 1- and d-GABOB species considered).
Schroeder et al., "Do Patients in Whom Myocardial Infarction Has Been Ruled Out Have a Better Prognosis After Hospitalization Than Those Surviving Infarction?", N. Eng. J. Med. 303, 1-5 (1980).
Wang et al., Tetrahedron: Asymmetry 1999, 10: pp. 1895-1901.
Bremer, J. Physio, Rev. 1983, 63: pp. 1420-1480.

* cited by examiner

*Primary Examiner*—Cecilia Tsang
*Assistant Examiner*—Aaron J Kosar
(74) *Attorney, Agent, or Firm*—Darby & Darby P.C.

(57) ABSTRACT

The present invention particularly relates to a chemoenzymatic process for the stereoselective preparation of both enantiomers of 3-hydroxy-4-trityloxy butanenitrile key intermediates for the preparation of (R)-GABOB by lipase mediated kinetic resolution of its racemates and their effective application in the enantioconvergent synthesis of (R)-GABOB.

8 Claims, No Drawings

ENANTIOCONVERGENT CHEMOENZYMATIC SYNTHESIS OF (R)-γ-AMINO-β-HYDROXYBUTYRIC ACID ((R)-GABOB)

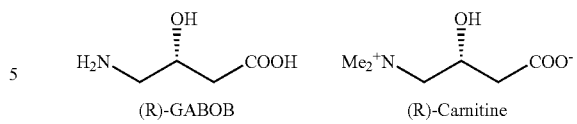

(R)-GABOB    (R)-Carnitine

FIELD OF THE INVENTION

The present invention relates to a chemoenzymatic enantioconvergent process for the stereoselective preparation of (R)-γ-amino-β-hydroxybutyric acid ((R)-GABOB).

The present invention particularly relates to a chemoenzymatic process for the stereoselective preparation of both enantiomers of 3-hydroxy-4-trityloxy butanenitrile key intermediates for the preparation of (R)-GABOB by lipase mediated kinetic resolution of its racemates and their effective application in the enantioconvergent synthesis of (R)-GABOB.

BACKGROUND OF THE INVENTION (R)-GABOB is a compound of tremendous pharmacological importance because of its biological function as a neuromodulator in the mammalian central nervous system. (Otsuka, M.; Obata, K.; Miyata, Y.; Yaneka, Y. *J. Neurochem* 1971, 18, 287; Otsuka, M.; Obata, K.; Miyata, Y. Advances in Biochemical Psychoparamacology Raven: New York, 1972, Vol 6, pp 61. ) It is known to function as an agonist of gamma-aminobutyric acid (GABA) and has been found to be a remarkable antiepileptic and hypotensive drug (Brehm, L.; Jacobsen, P.; Johansen, J. S.; Krogsgaard-Larsen, P. *J. Chem. Soc. Perkin Trans I* 1983, 1459). It has also been demonstrated to be effective in managing a variety of clinical conditions including schizophrenia and other character based illnesses (Chapoy, P. R.; Angelini, C.; Brown, W. J.; Stiff, J. E.; Shug, A. L.; Cederbaum, S. D.; *N. Engl. J. Med.* 1980, 303, 1389; Takano, S.; Yanase, M.; Sekiguchi, Y.; Ogasawara, K. *Tetrahedron Lett.* 1987, 28, 1783), epilepsy and other illnesses that result in severe convulsions. Its use for the correction of some clinical condition observed in children has also been explored. Moreover (R)-GABOB is a precursor for (R)-carnitine a vitamin like substance and plays an important role in converting stored body fat into energy. Its primary physiological function is to transport long chain fatty acids through the mitochondrial membrane into the cellular compartments for oxidation where these fats can be converted into energy (Fritz, I. B.; Kaplan, E.; Yu, K. T. N. *Am. J. Physiol.* 1962, 202, 117; Bremer, *J. Physiol. Rev.* 1983, 63, 1420; Brown, W. J.; Stiff, J. E.; Shug, A. L.; Cederbaum S. D.; *N. Engl. J. Med.* 1980, 303, 1389; McGarry, J. D.; Foster, D. W. *Ann. Rev. Biochem.* 1980, 49, 395) and is considered as a good antiobesity drug. The R-form of GABOB is shown to have greater biological activity than its S-enantiomer (Kurano; Masayasu; Miyaruoto; Shigetoshi; Shigeoka; Satoshi; Mori; Akitane. Japanese Patent 1976; *Chem. Abstr.* 1977, 86, 89207u; Ostsuka, M.; Obata, K.; Miyata; Y.; Yaneka, Y. *J. Neurochem.* 1971, 18, 287; Otsuka, M.; Miyata, Y. Advances in Biochemical Pysopharmacology, Raven: New York, 1972, Vol 6, pp 61; Kurono, M.; Miyamoto, S.; Shigeoka, S.; Mori, A. Japan, Kokai 76,100,026; *Chem. Abstr.* 1977, 86, 89207u).

In spite of the simple structure of GABOB a number of methods for their enantioselective preparation are described in the literature (Wang, G.; Hollingsworth, R. I. *Tetrahedron: Asymmetry* 1999, 10, 1895 and references cited therein). They have been prepared by optical resolution, asymmetric synthesis from natural products, catalytic asymmetrical synthesis and by employing enzymes in the key enantioselective step. Earlier approaches reported in the literature have either long reaction sequences thereby reducing the overall yield or have employed chiral starting material not in the chiral pool or have obtained the target compounds in low enantioselectivity. In view of the high biological importance associated with these compounds a more facile, efficient and cost effective approach has been investigated.

GABOB has four-carbon chain in its basic structural skeleton and retrosynthetic strategy reveals that enantiomerically pure 3-hydroxy-4-trityloxybutanenitrile or 3-acetyloxy-4-trityloxybutanenitrile can be excellent chiral building block for the synthesis of target molecule.

OBJECT OF THE INVENTION

The main objective of the present invention is to provide a chemoenzymatic process for the stereoselective preparation of both enantiomers of 3-hydroxy-4-trityloxy butanenitrile and their effective application in the preparation of (R)-GABOB through an enantioconvergent process.

SUMMARY OF THE INVENTION

The present invention provides a chemoenzymatic enantioconvergent process for the stereoselective preparation of (R)-GABOB which comprises of
  i) transesterifying 3-hydroxy-4-trityloxybutanenitrile and separating enantiomers obtained by lipase-mediated kinetic resolution in the presence of lipase and vinyl acetate;
  ii) transforming optically pure (R)-3-acetyloxy-4-trityloxybutanenitrile to (R)-GABOB; and
  iii) transforming (s)-3-hydroxy-4-trityloxybutanenitrile to (R)-GABOB.

In one embodiment of the invention, the acetylating agent is selected from the group consisting of vinylacetate and isopropenyl acetate have been employed for the transesterification of 3-hydroxy-4-trityloxybutanenitrile.

In another embodiment of the invention the lipase is selected from the group consisting of *Psuedoinonas cepacia* lipase immobilized on modified ceramic particles (PS-C), *Pseudomonas cepacia* lipase immobilized on diatomite (PS-D), *Pseudomonas cepacia* (PS), *Pseudomonas flucrescens* lipase (AK), immobilized lipase from *Mucor meihei* (Lipozyme), *Candida rugosa* lipase (CRL), and *Candida antartica* lipase immobilized in Sol-Gel-AK on sintered glass (CAL B).

In another embodiment of the invention, step (i) is effected in the presence of a solvent selected from the group consisting of diisopropylether, hexane, diethyl ether, toluene, chloroform, acetone, tetrahydrofuran and dioxane.

In another embodiment of the invention, step (i) is effected in the presence of one or more base additives selected from the group consisting of pyridine, triethylamine, DMAP, and 2,6-lutidine.

In another embodiment of the invention, recycling of resolved enantiomers is avoided since the enantiomeric excess of both enantiomers is >99%.

In another embodiment of the invention, (R)-3-acetylxoy-4-trityloxybutanenitrile is transformed to (R)-3-hydroxy-4-tosyloxybutanenitrile by treating with $K_2CO_3$ and p-toluenesulphonic acid in methanol and then with p-toluenesulphohyl chloride and $Et_3N$ in the presence of $Bu_2SnO$ in dichloromethane.

In another embodiment of the invention, (R)-3-hydroxy-4-tosyloxybutanenitrile is transformed to (R)-GABOB in step (iii) in a single-pot by treating with aqueous ammonia and then with dil. HCl.

In another embodiment of the invention, (s)-3-hydroxy-4-trityloxybutanenitrile is transformed to (s)-5-trityloxymethyl-1,3-oxazolidine-2-one by treating with ammonia and hydrogen peroxide and then with $Pb(OAc)_4$ in pyridine.

In another embodiment of the invention, (S)-5-trityloxymethyl-1,3-oxazolidine-2-one is transformed to (S)-5-tosyloxymethyl-1,3-oxazolidine-2-one by treating with p-toluenesulphonic acid in methanol and later with p-toluenesulphonyl chloride and $Et_3N$ in dichloromethane.

In another embodiment of the invention, (S)-5-tosyloxymethyl-1,3-oxazolidine-2-one is transformed to (R)-5-cyanomethyl-1,3-oxazolidine-2-one by treating with NaCN which is then converted to (R)-GABOB by reacting with hydrochloric acid.

DETAILED DESCRIPTION OF THE INVENTION

The present invention provides a chemoenzymatic enantioconvergent process for the stereoselective preparation of (R)-GABOB which comprises of
(i) transesterifying 3-hydroxy-4-trityloxybutanenitrile and separating enantiomers obtained by lipase-mediated kinetic resolution in the presence of lipase and vinyl acetate;
(ii) transforming optically pure (R)-3-acetyloxy-4-trityloxybutanenitrile to (R)-GABOB; and
(iii) transforming (S)-3-hydroxy-4-trityloxybutanenitrile to (R)-GABOB.

The acetylating agent selected from the group consisting of vinylacetate and isopropenyl acetate have been employed for the transesterification of 3-hydroxy-4-trityloxybutanenitrile. The lipase is selected from the group consisting of *Psuedomonas cepacia* lipase immobilized on modified ceramic particles (PS-C), *Pseudomonas cepacia* lipase immobilized on diatomite (PS-D), *Pseudomonas cepacia* (PS), *Pseudomonas fluorescens* (AK), immobilized lipase from *Mucor meihei* (Lipozyme), *Candida rugosa* lipase (CRL), and *Candida antartica* lipase immobilized in Sol-Gel-AK on sintered glass (CAL B). Step (i) is effected in the presence of a solvent selected from the group consisting of diisopropylether, hexane, diethyl ether, toluene, chloroform, acetone, tetrahydrofuran and dioxane and in the presence of various additives if desired. The additives used include one or more base additives selected from the group consisting of pyridine, triethylamine, DMAP, and 2,6-lutidine. Recycling of resolved enantiomers is avoided since the enantiomeric excess of both enantiomers is >99%.

(R)-3-acetylxoy-4-trityloxybutanenitrile is transformed to (R)-3-hydroxy-4-tosyloxybutanenitrile by treating with $K_2CO_3$ and p-toluenesulphonic acid in methanol and then with p-toluenesulphohyl chloride and $Et_3N$ in the presence of $Bu_2SnO$ in dichloromethane. (R)-3-hydroxy-4-tosyloxybutanenitrile is transformed to (R)-GABOB in step (iii) in a single-pot by treating with aqueous ammonia and then with dil. HCl.

(S)-3-hydroxy-4-trityloxybutanenitrile is transformed to (S)-5-trityloxymethyl-1,3-oxazolidine-2-one by treating with ammonia and hydrogen peroxide and then with $Pb(OAc)_4$ in pyridine. (S)-5-trityloxymethyl-1,3-oxazolidine-2-one is transformed to (S)-5-tosyloxymethyl-1,3-oxazolidine-2-one by treating with p-toluenesulphonic acid in methanol and later with p-toluenesulphonyl chloride and $Et_3N$ in dichloromethane. (S)-5-tosyloxymethyl-1,3-oxazolidine-2-one is transformed to (R)-5-cyanomethyl-1,3-oxazolidine-2-one by treating with NaCN which is then converted to (R)-GABOB by reacting with hydrochloric acid.

As explained above, the present invention provides a chemoenzymatic enantioconvergent process for the preparation of (R)-GABOB through a lipase mediated kinetic resolution of racemic 3-hydroxy-4-trityloxybutanenitrile. The following schemes represent the preparation of enantiomerically pure (S)-3-hydroxy-4-trityloxy butanenitrile and (R)-3-acetyloxy-4-trityloxybutanenitrile and their successful application in the preparation of (R)-GABOB.

Scheme 1

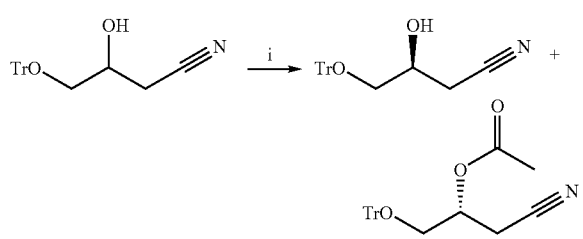

Reagents and conditions: i. PS-C, vinyl acetate, diisopropyl ether, 46° C.

Scheme 2

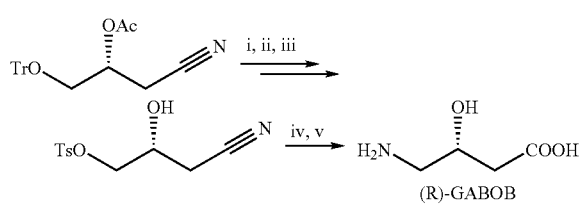

Reagents and conditions: i. $K_2CO_3$, MeOH; ii. PTSA, MeOH, rt.; iii. TsCl, $Et_3N$, $Bu_2SnO$, DCM; iv. aqueous ammonia, EtOH reflux; v. aqueous trimethylamine, EtOH reflux.

Scheme 3

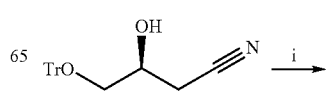

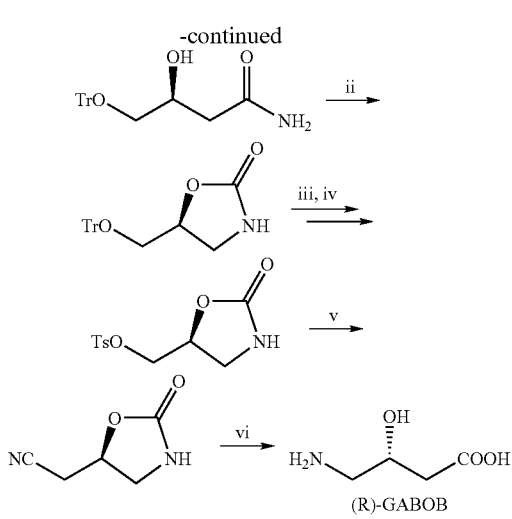

Reagents and conditions: i. H₂O₂, aq.NH₃, rt.; ii. Pb(OAc)₄, pyridine; iii. PTSA, MeOH, rt.; iv. TsCl, Et₃N, DCM; v. NaCN, MeOH—H₂O, reflux; vi. Conc. HCl, 80° C.

In the invention 3-hydroxy-4-trityloxybutanenitrile was prepared from 3-trityloxy-1,2-epoxypropane. 3-hydroxy-4-trityloxybutanenitrile was efficiently resolved by stereoselective acetylation in the presence of vinyl acetate and lipases and if desired, various additives.

The alcohol and the acetate formed in the kinetic resolution process are separated by column chromatography. The enantiomeric purities of the compounds were determined by HPLC employing a chiral column (Chiralcel OD). Absolute configurations were preliminarily presumed to be R for the acetate and S for the alcohol by the empirical rule for the stereo-preference of lipase and then later confirmed by comparison of their chiroptical and chromatographic properties with those of the compounds of known configuration.

Optically pure (R)-3-acetyloxy-4-trityloxybutanenitrile was converted to (R)-3-hydroxy-4-tosyloxybutanenitrile and later to (R)-GABOB. (S)-3-hydroxy-4-trityloxybutanenitrile has been converted to (S)-5-tosyloxymethyl-1,3-oxazolidine-2-one and later to (R) GABOB.

The process of the present invention is explained in detail below:

1. The racemic 3-hydroxy-4-trityloxybutanenitrile has been prepared by the ring opening of 3-tritiloxy-1,2-epoxypropane using NaCN in aqueous ethanol.
2. Racemic 3-hydroxy-4-trityloxybutanenitrile has been stereoselectively acetylated in the presence of various lipases in different solvents and in the presence of various acetylating agents.
3. Acetylation of racemic 3-hydroxy-4-trityloxybutanenitrile has also been studied in the presence of additives, lipases and acetylating agents.
4. Acetylating agents such as vinyl acetate and isopropenyl acetate have been used for lipase-catalyzed acetylation reaction.
5. Different lipases like *Pseudomnonas cepacia* lipase immobilized on modified ceramic particles (PS-C), *Pseudomonas cepacia* lipase immobilized on diatomite (PS-D), *Pseudomonas cepacia* (PS), *Pseudomonas fluorescens* lipase (AK), immobilized lipase from *Mucor meihei* (Lipozyme), *Candida rugosa* lipase (CRL), and *Candida antartica* lipase immobilized in Sol-Gel-AK on sintered glass (CAL B) have been screened for the kinetic resolution process.
6. Various solvents like diisopropylether, hexane, diethyl ether, toluene, chloroform, acetone, tetrahydrofuran and dioxane have been employed in this resolution process.
7. Various bases such as pyridine, triethylamine, DMAP, 2,6-lutidine etc., have been employed as additives in this resolution process.
8. Optically pure S alcohol and R acetate obtained after lipase-mediated resolution process have been separated by column chromatography.
9. The enatiomeric purities of the resolved alcohol and the ester has been determined by the HPLC employing chiral OD column.
10. Optically pure (R)-3-acetyloxy-4-trityloxybutanenitrile has been transformed to (R)-3-hydroxy-4-tosyloxybutanenitrile on treating with K₂CO₃ and p-toluene-sulphonic acid in MeOH and then with p-toluenesulphonylchloride, Bu₂SnO, Et₃N in dichloromethane.
11. Optically pure (R)-3-hydroxy-4-tosyloxybutanenitrile has been transformed to (R)-GABOB in a single-pot on treating with aq.NH₃ and then with dil.HCl.
12. Optically pure (R)-GABOB thus obtained has been purified by ion-exchange chromatography and by recrystalization.
13. Optically pure (S)-3-hydroxy-4-trityloxybutanenitrile has been transformed to (S)-hydroxy-4-trityloxybutanamide on treating with aq. NH₃ in the presence of H₂O₂ which in turn has been transformed to (S)-5-trityloxymethyl-1,3-oxazolidine-2-one on treating with Pb(OAc)₄ in pyridine.
14. (S)-5-trityloxymethyl-1,3-oxazolidine-2-one has been treated with p-toluenesulphonic acid/MeOH and later with p-toluenesulphonylchloride and Et₃N in dichloromethane to obtain (s)-5-tosyloxymethyl-1,3-oxazolidine-2-one.
15. (S)-5-tosyloxymethyl-1,3-oxazolidine-2-one has been treated with NaCN in aqueous-methanol to afford (R)-5-cyanomethyl-1,3-oxazolidine-2-one.
16. (R)-5-cyanomethyl-1,3-oxazolidine-2-one on treating with hydrochloric acid at 80° C. afforded optically pure (R)-GABOB.
17. Optically pure (R)-GABOB thus obtained has been purified by ion-exchange chromatography and by recrystalization.

The following examples are given by way of illustration and they should not be construed to limit the scope of the present invention.

EXAMPLE 1

(±)-3-Hydroxy-4-trityloxybutanenitrile

To a stirring solution of 3-trityloxy-1,2-epoxypronane (15.80 g, 50.00 mmol) in 50 mL of ethanol was added 150 mL of H₂O and NaCN (2.94 g, 60.00 mmol). The resultant reaction mixture was stirred overnight at room temperature and on completion of the reaction (TLC), the reaction mixture was concentrated to about 50% of the total volume under reduced pressure. The residue was extracted with ethyl acetate (3×125 mL), washed with brine and dried over anhydrous Na₂SO₄. Evaporation of the solvent and purification of the residue by column chromatography employing EtOAc-hexane (25:75) as eluent afforded 3-hydroxy-4-trityloxybutanenitrile in 82% yield. IR (Neat) 3506, 3043, 2996, 2918, 2855, 2275, 1106, 1051 cm$^{-1}$; $^1$HNMR (200 MHz, CDCl$_3$) δ 2.45-2.56 (m, 2H), 3.27 (d, 2H,J=5.2 Hz), 3.92-4.02 (m, 1H), 7.23-7.41 (m, 15H); Mass (EI) 259, 243, 165, 105, 77.

EXAMPLE 2

(±)-3-Acetyloxy-4-triphenylmethoxybutanenitrile

To (±)-3-hydroxy-4-trityloxybutane-nitrile (1.03 g, 3.00 mmol) under N$_2$ was added acetic anhydride (1.53 g, 15.00 mmol) and pyridine (0.26 g, 3.30 mmol) and the resultant mixture was stirred overnight at room temperature. After completion of the reaction (TLC) the reaction mixture was diluted with ethyl acetate (25 mL) and treated with 1N HCl (20 mL). The organic layer was separated, washed with brine and dried over anhydrous Na$_2$SO$_4$. The solvent was evaporated and the residue was purified by column chromatography employing EtOAc-hexane (15:85) as eluent to afford the required 3-acetyloxy-4-trityloxybutanenitrile in nearly quantitative yield. IR (KBr) 3466, 3066, 3019, 2925, 2863, 2235, 1741, 1223, 1004 cm$^{-1}$; $^1$HNMR (300 MHz, CDCl$_3$) δ 2.09 (s, 3H), 2.76 (d, 2H, J=5.69, 5.79 Hz), 3.92-4.02 (m, 1H), 7.23-7.41 (m, 15H); Mass (EI) 259, 243, 165, 105, 77.

EXAMPLE 3

Procedure for Resolution of 3-hydroxy-4-trityloxybutanenitrile

To a solution of 3-hydroxy-4-trityloxybutanenitrile (1.50 g) in diisopropyl ether (160 mL) were successively added lipase (1.50 g) and vinyl acetate (6 equivalents) and shaken at room temperature in orbital shaker. After about 50% completion of the reaction as indicated by the HPLC analysis the reaction mixture was filtered and the residue was washed thrice with diisopropyl ether. The combined organic layers were evaporated under reduced pressure and purification was accomplished by column chromatography employing EtOAc-hexane (20:80) as eluent to afford the corresponding (R)-acetate followed by (S)-alcohol. (S)-3-Hydroxy-4-trityloxybutanenitrile: m.p. 144-146° C.; [α]$^{29}_D$=−7.64 (c 1.5, CHCl$_3$); IR, NMR and Mass spectral data are identical to racemic 3-hydroxy-4-trityloxybutanenitrile. (R)-3-Acetyloxy-4-tritylxoybutanenitrile: m.p. 155-158° C.; [α]$^{29}_D$=+24.44 (c 1.35, CHCl$_3$); IR, NMR and Mass spectral data are identical to racemic 3-acetyloxy-4-trityl-oxybutanenitrile.

EXAMPLE 4

Chiral HPLC Analysis

HPLC analysis was performed on an instrument that consisted of a Shimadzu LC-10AT system controller with a SPD-10A fixed wavelength UV monitor as a detector. Analysis were performed by employing chiral column (Chiralcel OD, Daicel) with hexane:isopropanol (90:10) as the mobile phase at a flow rate of 0.5 mL/min and monitored at UV-254 nm. Racemic acetate was prepared as described in example 2 as an authentic sample for comparison on HPLC.

EXAMPLE 5

(R)-3Hydroxy-4-tosyloxybutanenitrile

To a solution of (R)-3-acetyloxy-4-trityloxybutanenitrile (3.85 g, 10.00 mmol) in methanol (40 mL) was added K$_2$CO$_3$ (6.90 g, 50.00 mmol) and stirred at room temperature for 2 h. After completion of the reaction as indicated by TLC, K$_2$CO$_3$ was filtered and the residue was washed with 20 mL of methanol. To the combined filtrates was added p-toluenesulphonic acid (7.61 g, 40.00 mmol) and stirred overnight at room temperature. After completion of the reaction, the solvent in the reaction mixture was evaporated and the residue was purified by column chromatography to obtain 3,4-dihydroxybutanenitrile. To the above obtained 3,4-dihydroxybutanenitrile was added dry dichloromethane (100 mL), dibutyltinoxide (0.50 g, 2.00 mmol) and p-toluenesulphonyl chloride (2.29 g, 12.00 mmol) and stirred for about 1 h. The reaction mixture was treated with 100 mL of water, the organic layer was separated and the aqueous layer was extracted with dichloromethane (125 mL). The combined organic layers were dried over Na$_2$SO$_4$ and evaporated to leave a residue, which was purified by column chromatography employing EtOAc-hexane (30:70) as eluent to afford the title compound in 60% yield. [a]$^{26}_D$=+13.5 (c 1.45, EtOH); IR (Neat) 3474, 3059, 2933, 2902, 2220, 1584, 1349, 1169, 1098, 996 cm$^{-1}$; $^1$HNMR (300 MHz, CDCl$_3$) δ 2.48 (s, 3H), 2.52-2.67 (m, 2H), 4.06 (d, 2H, J=5.4 Hz), 4.15-4.22 (m, 1H), 7.38 (d, 2H,j=8.3 Hz), 7.80 (d, 2H, J=8.3 Hz); Mass (EI) 255 (M$^+$), 173, 155, 139, 122, 91.

EXAMPLE 6

(R)-GABOB

To a solution of (R)-3-hydroxy-4-tosyloxybutanenitrile (3.50 g, 13.70 mmol) in ethanol (40 mL) was added excess aq.NH$_3$, refluxed overnight and the solvents in the reaction mixture were evaporated. To the resulting residue was added conc. HCl and heated to 80° C. for 6 h after evaporation of the solvent the residue containing crude (R)GABOB was purified over an ion exchange column chromatography (Amberlite IR-120 H$^+$). The column was first eluted with water until the fractions were neutral and later with 10% NH$_4$OH. Evaporation of the basic fractions gave thick oil, which was dissolved in minimum amount of water and absolute ethanol was added to provide (R)-GABOB as a white solid (84%). Recrystalization of the (R)-GABOB from water-ethanol provided pure (R)-GABOB as white crystals (73%) yield. m.p.211-213° C.; [a]$^{28}_D$=−20.7 (c 1.0, H$_2$O); $^1$HNMR (200 MHz, D$_2$O ) δ2.43 (d, 2H,J =5.9 Hz), 2.95 (dd, 1H, J$_1$=9.66 Hz, J$_2$=13.38 Hz), 3.18 (dd, 1H, J$_1$=3.72 Hz,J$_2$=13.38 Hz), 4.10-4.30 (m, 1H); $^{13}$CNMR (50 MHz, D$_2$O) δ 42.3, 44.0, 65.5, 178.5; Mass (EI) 118 (M$^+$−H), 74, 60, 43.

EXAMPLE 7

(S)-3-Hydroxy-4-triphenylmethoxy butanamide

To a stirring solution of (S)-3-hydroxy-4-trityloxybutanenitrile (5.15 g, 15.01 mmol) in 15 mL of ethanol at room temperature was added aqueous NH$_3$ (50 mL) and H$_2$O$_2$ (100 vol.) (34 mL, 300.00 mmol) was added in portions while maintaining the temperature of the reaction mixture below 25° C. After complete addition, the resultant reaction mixture was stirred vigorously at 25-30° C. and the reaction progress was monitored by TLC. On completion of the reaction (overnight) as indicated by the TLC, the reaction volume was concentrated to about 50% of the original volume under reduced pressure and the resultant mixture was extracted with dichloromethane (3×75 mL). The combined organic layers were dried over anhydrous $Na_2SO_4$ and the solvent was evaporated to leave a residue, which was purified by column chromatography employing EtOAc-hexane (80:20) as eluent to afford (S)-3-hydroxy-4-trityloxy butanamide in almost quantitative yield. m.p. 96-100° C.; $[\alpha]^{27}{}_D$=−18.08 (c 1.0, MeOH); IR (KBr) 3467, 3349, 3012, 2980, 2918, 2839, 1671, 1098, 1076 $cm^{-1}$; $^1$HNMR (300 MHz, $CDCl_3$) δ 2.36 (d, 2H, J=6.5 Hz), 3.13-3.16 (m, 2H), 3.28 (6S, 1H), 4.11-4.15 (m, 1H), 5.44 (br, s, 1H), 7.18-7.38 (m, 9H), 7.39-7.42 (m, 6H); Mass (EI) 361, 259, 243, 165, 77.

EXAMPLE 8

(S)-5-Trityloxymethyl-1,3-oxazolidine-2-one

To a solution of (S)-3-hydroxy-4-trityloxy butanamide (4.33 g, 12.00 mmol) in pyridine (25 mL) was added $Pb(OAc)_4$ (7.45 g, 16.80 mmol) and the resultant reaction mixture was stirred under $N_2$ at room temperature for 1 h. On completion of the reaction as indicated by the TLC, the reaction mixture was taken up in dichloromethane (100 mL) and then treated with 1N HCl (125 mL). The resultant reaction mixture was filtered through a celite pad and the residue was washed thrice with dichloromethane (50 mL). The organic layer from the combined filtrates and washings were separated and the aqueous layer was extracted with dichloromethane (2×100 mL). The organic layer free from pyridine was washed with brine, dried over anhydrous $Na_2SO_4$ and -concentrated to leave a residue of crude oxazolidinone which was purified by column chromatography employing EtOAc-hexane (50:50) as eluent to afford pure 5-trityloxymethyl-1,3-oxazolidine-2-one in 85% yield. $[\alpha]^{26}{}_D$=+25.0 (c 1.0, MeOH); IR (KBr) 3247, 2933, 2886, 2824, 1741, 1012, 949 $cm^{-1}$; $^1$HNMR (300 MHz, $CDCl_3$) δ 3.24 (dd, 1H, $J_1$=4.5 Hz, $J_2$=10.4 Hz), 3.36-3.48 (m, 3H), 3.75-3.64 (m, 1H), 4.71-4.77 (m, 1H), 5.27 (br, s, 1H), 7.21-7.44 (m, 9H), 7.46-7.47 (m, 6H); Mass (EI) 274, 258, 243, 183, 165, 105, 77.

EXAMPLE 9

(S)-5-Hydroxymethyl-1,3-oxazolidine-2-one

To a stirring solution of (S)-5-trityloxymethyl-1,3-oxazolidine-2-one (7.18 g, 20.00 mmol) in 60 mL of methanol at room temperature was added p-toluenesulphonic acid (7.16 g, 40.00 mmol) and stirring continued for overnight. After completion of the reaction (TLC), the solvent in the reaction mixture was evaporated and the residue was purified by column chromatography employing MeOH-EtOAc (5:95) as eluent to afford pure 5-hydroxymethyl-1,3-oxazolidine-2-one in 88% yield. m.p. 70-73° C.; $[a]^{27}{}_D$=+32.83 (c 0.6, EtOH); $^1$HNMR (200 MHz, DMSO ($d_6$)) δ 3.35-3.75 (m, 4H), 4.50-4.64 (m, 1H), 4.85 (br s, 1H).

EXAMPLE 10

(S)-5tosyloxymethyl-1,3-oxazolidine-2-one p-Toluenesulphonyl chloride (2.74 g, 14.36 mmol) and $Et_3N$ (1.45 g, 14.36 mmol) were added to 5-hydroxymethyl-1,3-oxazolidine-2-one (1.40 g, 11.97 mmol) dispersed in 20 mL of dichloromethane and stirred overnight at room temperature under $N_2$. After completion of the reaction (TLC), the solvent in the reaction mixture was evaporated and the residue was purified by column chromatography employing EtOAc-hexane (70:30) as eluent to afford 5-tosyloxymethyl-1,3-oxazolidine-2-one in 80% yield. m.p. 96-99° C.; $[\alpha]^{27}{}_D$=+45.40 $CHCl_3$); IR (KBr) 3302, 2980, 2925, 2871, 1757, 1694, 1357, 1184, 1090, 996, 965 $cm^1$; $^1$HNMR (200 MHz, $CDCl_3$) δ 2.47 (s, 3H), 3.40-3.50 (m, 1H), 3.64-3.74 (m, 1H), 4.14 (d, 2H, J=4.4 Hz), 4.71-4.82 (m, 1H), 7.35 (d, 2H, J=8.2 Hz), 7.78 (d, 2H, J=8.2 Hz); Mass (EI) 271, 207, 173, 155, 139, 91.

EXAMPLE 11

(R)-5-Cyanomethyl-1,3-oxazolidine-2-one

To a stirring solution of (S)-5-tosyloxymethyl-1,3-oxazolidine-2-one (0.54 g, 1.99 mmol) in MeOH-water (15-3 mL) was added NaCN (0.39 g, 8.00 mmol) at room temperature and then heated to reflux for 4 h. After completion of the reaction, solvent in the reaction mixture was completely evaporated and the residue was purified by column chromatography employing EtOAc-hexane (70:30) as eluent to afford pure 5-cyanomethyl-1,3-oxazolidine-2-one in 70% yield. $[\alpha]^{26}{}_D$=+4.5 (c 1.0, MeOH); IR (Neat) 3349, 2918, 2839, 2243, 1710, 1255, 1051 $cm^1$; $^1$HNMR (200 MHz, $CD_3OD$) δ 2.57 (d, 2H, J=6.6 Hz), 3.20-3.55 (m, 2H), 4.00-4.18 (m, 1H).

EXAMPLE 12

(R)-4-Amino-3-hydroxybutanoic acid (GABOB)

A mixture of (R)-5-cyanomethyl-1,3-oxazolidine-2-one (0.15 g, 1.2 mmol) and conc. HCl (15 mL) was stirred and heated to 80-90° C. for 6 h. After completion of the reaction, as indicated by the TLC the solvent in the reaction mixture was evaporated and the residue was purified by an ion exchange column chromatography (Amberlite IR 120 $H^+$). First eluted with water until the fractions collected was neutral and later with 10% $NH_4OH$. The solvent in the basic fractions were evaporated and redissolved in minimum amount of $H_2O$ and triturated with EtOH to obtain (R)-GABOB as a colourless solid after evaporation of the solvent. m.p. 209-212° C.; $[\alpha]^{28}{}_D$=−20.1 (c 1.0, $H_2O$); $^1$HNMR, $^{13}$CNMR and Mass data are identical to data of (R)-GABOB prepared from (R)-3-acetoxy-4-trityloxybutanenitrile.

The main advantages of the present invention are:

β-Hydroxy nitrites or vicinal cyanohydrins are important and versatile compounds in organic synthesis as these hydroxy nitriles in optically pure form provides a number of opportunities for synthetic manipulations leading to a wide range of chiral synthons like amino alcohols, hydroxy amides, hydroxy acids, hydroxy esters etc. Moreover, the high functionality of the 3-hydroxy4-trityloxybutanenitrile (trityloxy group, hydroxyl group, nitrile group) makes it a very useful intermediate for synthesis of a variety of optically pure compounds of biological importance. Also, the intermediates obtained in this process are of utmost optical purity, which is essential for the preparation of target biologically important compounds. Moreover, this being an enantioconvergent process the unwanted enantiomer after the resolution process (S-enantiomer) has also been successfully employed in the preparation of the target molecule thereby increasing the overall yield of the process.

We claim:

1. A chemoenzymatic enantioconvergent process for the stereoselective preparation of (R)-γ-amino-β-hydroxybutyric acid, which comprises the steps of:
   (a.) contacting 3-hydroxy-4-trityloxybutanenitrile with a lipase and an acylating agent;
   (b.) in the presence of said lipase and said acetylating agent, transesterifying the 3-hydroxy-4-trityloxybutanenitrile and obtaining by lipase-mediated kinetic resolution (R)-3-acetyloxy-4-trityloxybutanenitrile and (S)-3-hydroxy-4-trityloxybutanenitrile enantiomers;
   (c.) transforming the (R)-3-acetyloxy-4-trityloxybutanenitrile enantiomer to (R)-γ-amino-β-hydroxybutyric acid; and,
   (d.) transforming the (S)-3-hydroxy-4-trityloxybutanenitrile enantiomer to (R)-γ-amino-β-hydroxybutyric acid.

2. The process of claim 1 wherein the acetylating agent is selected from vinyl acetate or isopropenyl acetate.

3. The process of claim 1 wherein the lipase is selected from the group consisting of *Pseudomonas cepacia* lipase immobilized on modified ceramic particles (PS-C), *Pseudomonas cepacia* lipase immobilized on diatomite (PS-D), lipase obtained from *Pseudomonas cepacia* (PS), lipase obtained from *Pseudomonas fluroescens* (AK), immobilized lipase obtained from *Mucor meihei*, lipase obtained from *Candida rugosa* (CRL), and *Candida antarctica* lipase immobilized in Sol-Gel-AK on sintered glass (CAL B).

4. The process of claim 1, wherein in step (a) the 3-hydroxy-4-trityloxybutanenitrile, lipase, and acylating agent are contacted in a solvent, wherein said solvent is selected from the group consisting of diisopropylether, hexane, diethyl ether, toluene, chloroform, acetone, tetrahydrofuran, and dioxane.

5. The process of claim 1 wherein in steps (a) and/or (b) one or more base additive is contacted with the 3-hydroxy-4-trityloxybutanenitrile, lipase, and acylating agent, wherein said one or more base additive is selected from the group consisting of triethylamine, pyridine, 4-dimethylaminopyridine, and 2,6-lutidine.

6. The process of claim 1 wherein recycling of resolved enantiomers is avoided.

7. The process of claim 1 wherein the transforming step (c) comprises:
   (i.) contacting (R)-3-acetyloxy-4-trityloxybutanenitrile first with potassium carbonate and p-toluenesulphonic acid in methanol and then with p-toluenesulphonyl chloride and triethylamine in the presence of dibutyltin oxide in dichloromethane to produce (R)-3-hydroxy-4-tosyloxybutanenitrile;
   (ii.) contacting (R)-3-hydroxy-4-tosyloxybutanenitrile with aqueous ammonia and then with dilute hydrochloric acid in a single-pot to produce (R)-γ-amino-β-hydroxybutyric acid; and,
   (iii.) recovering (R)-γ-amino-β-hydroxybutyric acid.

8. The process of claim 1 wherein the transforming step (d) comprises:
   (i.) contacting (S)-3-hydroxy-4-trityloxybutanenitrile with ammonia and hydrogen peroxide and then with lead(IV) acetate in pyridine to produce (S)-5-trityloxymethyl-1,3-oxazolidine-2-one;
   (ii.) contacting (S)-5-trityloxymethyl-1,3-oxazolidine-2-one with p-toluenesulphonic acid in methanol and then with p-toluenesulphonyl chloride and $Et_3N$ in dichloromethane to produce (S)-5-tosyloxymethyl-1,3-oxazolidine-2-one;
   (iii.) contacting (S)-5-tosyloxymethyl-1,3-oxazolidine-2-one with sodium cyanide to produce (R)-5-cyanomethyl-1,3-oxazolidine-2-one;
   (iv.) treating (R)-5-cyanomethyl-1,3-oxazolidine-2-one with hydrochloric acid to produce (R)-γ-amino-β-hydroxybutyric acid; and,
   (v.) recovering (R)-γ-amino-β-hydroxybutyric acid.

* * * * *